United States Patent
Ardenkjaer-Larsen et al.

(10) Patent No.: US 7,557,573 B2
(45) Date of Patent: Jul. 7, 2009

(54) NMR-BASED METHODS FOR DETECTING LIGANDS, WHERE THE LIGAND OR TARGET ARE HYPERPOLARIZED AND THE NMR-SPECTRUM IS COMPARED WITH A REFERENCE SPECTRUM OF THE LIGAND OR TARGET

(75) Inventors: Jan-Henrik Ardenkjaer-Larsen, Malmo (SE); Herbert Baumann, Uppsala (SE); Graham John Cotton, Edinburgh (GB); Klaes Golman, Malmo (SE); Mark Howard, Canterbury (GB); Mathilde H. Lerche, Malmo (SE); Rolf Servin, Malmo (SE); Mikkel Thaning, Malmo (SE); Jan Wolber, Malmo (SE)

(73) Assignee: GE Healthcare AS, Oslo (NO)

( * ) Notice: Subject to any disclaimer, the term of this patent is extended or adjusted under 35 U.S.C. 154(b) by 495 days.

(21) Appl. No.: 10/537,235

(22) PCT Filed: Nov. 27, 2003

(86) PCT No.: PCT/NO03/00396

§ 371 (c)(1),
(2), (4) Date: Jan. 10, 2006

(87) PCT Pub. No.: WO2004/051300

PCT Pub. Date: Jun. 17, 2004

(65) Prior Publication Data

US 2006/0171891 A1    Aug. 3, 2006

(30) Foreign Application Priority Data

Nov. 29, 2002  (NO)  ................................. 20025738

(51) Int. Cl.
*G01V 3/00* (2006.01)
(52) U.S. Cl. ...................................... 324/309; 324/307
(58) Field of Classification Search ......... 324/300–322; 600/407–422
See application file for complete search history.

(56) References Cited

U.S. PATENT DOCUMENTS

| 6,652,833 B2 * | 11/2003 | Pines et al. ................... 424/9.3 |
| 6,818,202 B2 * | 11/2004 | Pines et al. ................... 424/9.3 |
| 2002/0037253 A1 | 3/2002 | Pines et al. |
| 2003/0077628 A1 * | 4/2003 | Homans et al. ................. 435/6 |
| 2003/0165431 A1 * | 9/2003 | Pines et al. ................... 424/9.3 |
| 2005/0113453 A1 * | 5/2005 | Scanlan et al. ............... 514/567 |

FOREIGN PATENT DOCUMENTS

| DE | 10160177 | 6/2003 |
| WO | 97/18471 | 5/1997 |
| WO | 99/35508 | 7/1999 |
| WO | 00/62074 | 10/2000 |
| WO | 01/63267 | 8/2001 |
| WO | 02/33406 | 4/2002 |
| WO | 03/057258 | 7/2003 |
| WO | 03/096044 | 11/2003 |

OTHER PUBLICATIONS

Medek, et.al., "The use of differential Chemical Shifts for Determining the Binding Site Location and Orientation of Protein-Bound Ligands" J. Am. Chem. Soc. 2000, 122 1241-1242.
Chen, et.al., "NOE Pumping: A Novel NMR Technique for Identification of Compounds with Binding Affinity to Macromolecules" J. Am. Chem. Soc. 1998, 120, 10258-10259.
Chen, et.al., "NOE Pumping. 2. A Novel NMR Technique for Identification of Compounds with Binding Affinity to Macromolecules by NMR" J. Am. Chem. Soc 2000, 122, 414-415.
Mayer, et.al., Characterization of Ligand Binding by Saturation Transfer Difference NMR Spectroscopy, Angew. Chem. Int. Ed. 1999, 38, No. 12 pp. 1784-1788.
Shuker, et.al., Discovering High-Affinity Ligands for Proteins: SAR by NMR, Science, vol. 274, Nov. 29, 1996 pp. 1531-1534.
International Search Report for PCT/NO2003/000396 dated May 2004.
International Preliminary Examination Report for PCT/NO2003/000396 dated Jul. 2004.
Jenkins, Bruce G. "Detection of Site-Specific Binding and Co-Binding of Ligands to Macromolecules Using 19F NMR" Life Sciences, vol. 48, pp. 1227-1240.

* cited by examiner

*Primary Examiner*—Brij B Shrivastav
(74) *Attorney, Agent, or Firm*—Robert F. Chisholm

(57) ABSTRACT

The invention relates to NMR-based methods comprising hyperpolarised ligands or targets for use in NMR-based assays.

9 Claims, No Drawings

NMR-BASED METHODS FOR DETECTING LIGANDS, WHERE THE LIGAND OR TARGET ARE HYPERPOLARIZED AND THE NMR-SPECTRUM IS COMPARED WITH A REFERENCE SPECTRUM OF THE LIGAND OR TARGET

This application is a filing under 35 U.S.C. 371 of international application number PCT/NO2003/000396, filed Nov. 27, 2003, which claims priority to application number 20025738 filed Nov. 29, 2002, in Norway the entire disclosure of which is hereby incorporated by reference.

The invention relates to NMR-based methods comprising hyperpolarised ligands or targets for use in NMR-based assays.

The various genome sequencing projects currently underway are generating data at an enormous rate. Biomolecules encoded by the relevant gene sequences serve as target molecules (=targets) for the identification or the design of compounds that bind to them (=ligands), for example as natural ligands, as agonists or antagonists of a natural ligand, as an inhibitor, a substrate or target vector. As such, the identification of ligands is one of the first steps in drug discovery. Drug discovery comprises both the identification of lead compounds, i.e. compounds which exhibit high binding affinities to the chosen target and an optimisation process in which structure activity relationship between the target and the identified lead compound is studied in detail. In order to speed up drug discovery, libraries of synthetic or natural putative ligands are employed in a high-throughput screening process and the initial screening parameter is usually high binding activity of the ligand towards the target. The optimisation process focuses also on other important parameters of the ligand for being suitable as a future drug compound, such as chemical and metabolic stability, non-toxicity and optimal ADME (administration, distribution, metabolism and excretion) properties.

NMR is one of the most versatile tools in drug discovery today. Not only can NMR contribute in the identification of lead compounds, but it also facilitates the lead compound optimisation process by providing information about molecular structure and specific information about the binding of the ligand to the target. There are two different ways of collecting the information needed: monitoring NMR signals derived from the target or those arising from the ligand.

Chen et al., J. Am. Chem. Soc. 120 (1998), 10258-10259 describe the so-called "NOE-pumping technique" which relies on NOEs to transfer the signal from the target to a bound ligand. Non-equilibrium magnetisation is created by saturation of the ligand molecules. The signals from the ligands that do not bind to the target are suppressed by use of a diffusion filter (gradient strength and diffusion delay time).

Since the diffusion filter destroys the signals of the ligands before a NOE sequence is applied; only polarisation transfer from the target to a bound ligand can give polarisation to said ligand. When the ligand dissociates from the target, the polarisation transferred stays in the free ligand. The disadvantage of the method described is that due to rapid relaxation (especially $T_2$ relaxation) of the target the signal intensity is low, which reduces the sensitivity of the method. In addition, the applied diffusion filter requires an exchange between the ligand and the target. Hence, the affinity window in which interactions can be monitored is restricted and makes the method unsuitable for ligands with very high or very poor affinity.

A different way of performing the same experiment has also been suggested by A. Chen et al., J. Am. Chem. Soc. 122 (2000), 414-415. Here, the mechanism is reversed compared to the NOE-pumping technique, namely to detect signals transferred from a bound ligand to the target molecule. A $T_2$ filter is used to suppress the target signals while maintaining the signals from the ligands. The result is that signal intensity of the non-bound ligands decreases due to relaxation and NOE pumping. In order to detect this difference in signal intensity loss, a reference spectrum is necessary in which the signal intensity loss due to relaxation is recorded. The use of a $T_2$ filter limits this method to systems with relatively large differences in $T_2$ relaxation between the target and the ligand. This in turn requires the ligands to be in fast equilibrium between the free and bound state. This limits the range of affinities measurable with this method.

Mayer et al., Angew. Chem. Int. Ed. Engl. 38 (1999), 1784-1788 describe a method wherein a resolved target resonance is selectively saturated. This in turn results in the saturation of the entire target molecule and any ligand bound thereto due to efficient spin diffusion mechanisms. Subsequently, a relaxation filter is applied allowing the sole observation of the affected ligand signals. A reference spectrum is recorded with off-resonance irradiation and subtracted to reveal the signals of the bound ligand. Since the intensities of the bound ligand can be translated into distances, the binding site may be mapped. The disadvantage of this method is that more complex mixtures can only be examined by using 2D NMR spectra. If only small amounts of target and/or ligand are available, the method becomes very time consuming. Moreover, high affinity ligands cannot be measured, due to the applied relaxation filter.

Shuker et al., Science 274 (1996), 1531-1534 describe the so-called SAR-by-NMR method (SAR=structure activity relationship) wherein chemical shift changes in a $^{15}$N-labeled target molecule are monitored as a difference between the free target molecule and a target molecule with a ligand bound thereto. These chemical shift changes are mapped on to the structure of the target and the binding sites are characterised. Individually identified ligands with affinity to different binding sites on the target can be chemically linked to result in an optimised high affinity ligand. The method is limited to $^{15}$N-labeled target molecules. Moreover, the spectral assignment of the target has to be known.

WO-A1-97/18471 discloses a method to screen putative ligands which is based on generating a first 2D $^{15}$N/$^{1}$H-NMR correlation spectrum from a $^{15}$N-isotopically enriched protein and a second 2D $^{15}$N/$^{1}$H-NMR correlation spectrum from the $^{15}$N-isotopically enriched protein/ligand complex. The protein spectrum changes are then used to identify the binding site of the ligand. Again this method is restricted to the $^{15}$N-isotopically enriched protein targets.

WO-A1-00/62074 discloses a similar method that is based on and restricted to $^{13}$C-isotopically enriched target molecules.

WO-A1-02/33406 discloses a method for identifying a binder molecule by using $^{13}$C/$^{15}$N-labeled proteins wherein the labeled amino acids at least once occur in direct vicinity in the protein, generating a first HNCO-type NMR spectrum of the labeled target and a second HNCO-type NMR spectrum of the labeled target/ligand complex. The changes in chemical shift are then used to identify putative binder molecules. The disadvantage of the method is due to its limitation to specially labeled protein target molecules.

The disadvantages encountered by the above-described prior art methods are due to background interference and/or sensitivity limitations. In order to suppress background signals, those methods involve the use of so-called NMR filters that for example may be used to selectively suppress signals from the target and the ligand, respectively. Such filters put strains on molecular sizes and binding affinity windows and hence limit prior art methods. Sensitivity limitations may be problematic for several reasons: In order to alleviate such limitations, large amounts of either target or ligand are needed. The large quantities of ligands needed for the methods described above may generate stringent solubility demands on the ligands tested and thereby make it even more difficult to design ligand libraries. In addition the reaction may therefore take place under conditions which differ from physiological conditions. The large quantities of target needed make those NMR-based assays very costly and even hinder some targets to be assayed, as they can not be expressed in large enough quantities. Low sensitivity further results in long experimental sampling, making the prior art methods very time consuming and thus not useful as high throughput methods.

Thus, there was a need to provide a NMR-based screening method that overcomes the disadvantages of the prior art as outlined above.

We have now surprisingly found a NMR-based method which overcomes the problems associated with the prior art, the method comprising generating a NMR spectrum of a mixture comprising at least one hyperpolarised ligand, a target and optionally at least one further ligand or a hyperpolarised target and at least one ligand and comparing said NMR spectrum with a reference spectrum of the at least one hyperpolarised ligand or the hyperpolarised target.

In a preferred embodiment, the NMR-based method is carried out by a) hyperpolarising at least one ligand or a target b) forming a mixture by contacting the at least one hyperpolarised ligand with a target or a target and at least one further ligand or the hyperpolarised target with at least one ligand c) generating a NMR spectrum of the mixture, and d) comparing said NMR spectrum with a reference spectrum of the at least one hyperpolarised ligand or the hyperpolarised target.

The advantages of the method according to the invention are that no background signals are present as only the hyperpolarised species—either the target or the ligand—is detected. This allows the collection of NMR data without the application of NMR filters. Thus, the affinity window is not restricted in the method of the invention. Further, smaller amounts of target or ligand molecules are necessary due to the strongly enhanced sensitivity of the method of the invention compared to prior art methods. This in turn makes the solubility demands of the target/ligand less stringent and makes it possible to perform the method at more physiological relevant concentrations. Because of the increased sensitivity, it is further possible to combine the screening and optimisation step in a drug discovery process by screening for potent drug compounds directly amongst a pool of less potent compounds without the need for drug optimisation. It is possible, yet not necessary to use isotopically enriched target or ligand molecules. Whether isotopically enriched molecules are employed or not is only related to the degree of sensitivity requested. Spectra generation according to the method of the invention may be done by one-dimensional NMR and the spectra may be acquired in a single scan. This makes the method extremely fast and thus suitable for using it in a high throughput screening process. It may further become sensible to simply screen individual ligand compounds rather than ligand libraries, thus obtaining more accurate and reliable information.

Terms used throughout this specification have their usually accepted meanings. In a more specific definition, "target, target molecule or target compound" means any biomolecule, preferably a biomolecule selected form the group consisting of proteins, glycoproteins, lipoproteins, nucleic acids, e.g. DNA or RNA, polypeptides, glycopolypeptides, lipopolypeptides, peptides and parts or fragments thereof. The target may be a naturally derived target, e.g. obtainable by isolation from a natural organism, preferably animals or human beings or obtained by expression by genetically modified microorganism, e.g. bacteria. Such targets may further be modified, e.g. by treating them with enzymes or chemical compounds. The target may as well be a chemically synthesised target such as a chemically synthesised DNA, RNA, peptide or polypeptide.

In a more specific definition "ligand, ligand molecule or ligand compound" means any molecule that may to bind to a target. The ligand may be a protein, a glycoprotein, a lipoprotein, a polypeptide, a glycopolypeptide, a lipopolypeptide, a peptide, a carbohydrate, a nucleic acid e.g. DNA or RNA or a part, a fragment or a complex thereof, or any other chemical compound of interest. Preferably, the ligand is a relatively small organic molecule, particularly a small organic molecule of less than 2000 Da. Specially preferred are drug molecules. The ligand may be a naturally derived ligand, e.g. obtainable by isolation from a natural organism, preferably from plants, animals or human beings or obtained by expression by genetically modified microorganisms, e.g. bacteria. Such ligands may further be modified, e.g. by treating them with enzymes or chemical compounds. The ligand may as well be a chemically synthesised compound such as a chemically synthesised DNA, RNA, peptide or polypeptide or a small organic molecule.

In the method according to the invention, at least one hyperpolarised ligand or target is used.

If a ligand is hyperpolarised, it may be one ligand (e.g. ligand A) or a mixture of different ligand molecules (e.g. ligands A, B, C . . . ), e.g. a ligand library.

The term "hyperpolarisation" means enhancing the nuclear polarisation of NMR active nuclei present in the ligand or the target, i.e. nuclei with non-zero nuclear spin. Preferred nuclei are $^{13}$C, $^{15}$N, $^{31}$P, $^{19}$F, and/or $^{1}$H.

Isotopically enriched ligands or targets can be employed. If non-enriched ligands or targets are employed, ligands or targets containing nuclear species occurring at high natural abundance such as $^{31}$P, $^{19}$F, and/or $^{1}$H are preferred. Isotopically enriched ligands or targets are preferably used in the method according to the invention. The enrichment may include either selective enrichments of one or more sites within the ligand or target molecule or uniform enrichment of all sites. Enrichment can be achieved by chemical synthesis or biological labelling, the latter being especially useful to isotopically enrich target molecules. Suitable techniques are known in the art. Briefly, a target molecule that is expressed by a (genetically modified) microorganism can be uniformly enriched by, e.g. growing the microorganism in a nutrient medium containing uniformly $^{13}$C- or $^{15}$N-enriched nutrients like $^{13}$C-enriched glucose or $^{15}$NH$_4$Cl. Selective enrichment can be achieved by growing the microorganism in a nutrient medium containing e.g. $^{13}$C- or $^{15}$N-enriched amino acids like alanine or leucine. The target will thus be specifically $^{13}$C-enriched at those amino acid residues contained within the expressed target. Preferably, ligand and target molecules are selectively isotopically enriched, preferably in positions with long $T_1$ relaxation time. Suitably, target and ligand molecules according to the invention are isotopically enriched molecules with an enrichment of at least 10%, most suitably at least 25%, preferably at least 75%, most preferably at least 90%, ideally approaching 100%.

In a preferred embodiment of the present invention, the ligand and target molecules are selectively enriched with $^{13}$C and/or $^{15}$N, preferably with $^{13}$C or $^{15}$N, particularly preferred with $^{13}$C.

There are several ways for hyperpolarising NMR active nuclei, preferred ways are polarisation transfer from a noble gas, "brute force", DNP and spin refrigeration, all explained below.

A preferred way for hyperpolarising the NMR active nuclei containing probe compounds according to the invention is the polarisation transfer from a hyperpolarised noble gas. Noble gases having non-zero nuclear spin can be hyperpolarised, i.e. have their polarisation enhanced over the equilibrium polarisation, e.g. by the use of circularly polarised light. A hyperpolarised noble gas, preferably $^3$He or $^{129}$Xe, or a mixture of such gases, may be used according to the present invention to effect hyperpolarisation of the NMR active nuclei present in the probe and/or test compounds. The hyperpolarisation may also be achieved by using an artificially enriched hyperpolarised noble gas, preferably $^3$He or $^{129}$Xe. The hyperpolarised gas may be in the gas phase, it may be dissolved in a liquid, or the hyperpolarised gas itself may serve as a solvent. Alternatively, the gas may be condensed onto a cooled solid surface and used in this form, or allowed to sublime. Either of these methods may allow the necessary intimate mixing of the hyperpolarised gas with the molecule to be hyperpolarised. In some cases, liposomes or microbubbles may encapsulate the hyperpolarised noble gas.

Another preferred way for hyperpolarising NMR active nuclei according to the invention is that polarisation is imparted to said NMR active nuclei by thermodynamic equilibration at a very low temperature and high field. Hyperpolarisation compared to the operating field and temperature of the NMR spectrometer is effected by use of a very high field and very low temperature (brute force). The magnetic field strength used should be as high as possible, suitably higher than 1 T, preferably higher than 5 T, more preferably 15 T or more and especially preferably 20 T or more. The temperature should be very low, e.g. 4.2 K or less, preferably 1.5 K or less, more preferably 1.0 K or less, especially preferably 100 mK or less.

Another preferred way for hyperpolarising NMR active nuclei according to the invention is the DNP (dynamic nuclear polarisation) method effected by a DNP agent. DNP mechanisms include the Overhauser effect, the solid effect and the thermal mixing effect. Many known paramagnetic compounds may be used as DNP agents, e.g. transition metals such as chromium (V) ions, organic free radicals such as nitroxide radicals and trityl radicals (WO-A-98/58272) or other molecules having associated free electrons. Preferably, radicals with low relaxivity are used as DNP agents. Where the DNP agent is a paramagnetic free radical, the radical may be conveniently prepared in situ from a stable radical precursor by a radical-generating step shortly before the polarisation, or alternatively by the use of ionising radiation. During the DNP process, energy, normally in the form of microwave radiation, is provided, which will initially excite the paramagnetic species. Upon decay to the ground state, there is a transfer of polarisation to the NMR active nuclei of the target material. The method may utilise a moderate or high magnetic field and very low temperature, e.g. by carrying out the DNP process in liquid helium and a magnetic field of about 1 T or above. Alternatively, a moderate magnetic field and any temperature at which sufficient NMR enhancement is achieved in order to enable the desired studies to be carried out may be employed. The method may be carried out by using a first magnet for providing the polarising magnetic field and a second magnet for providing the primary field for MR spectroscopy. Alternatively, both DNP polarisation and NMR spectroscopy may be carried out in a single magnet.

Another preferred way for hyperpolarising NMR active nuclei according to the invention is the spin refrigeration method. This method covers spin polarisation of a solid compound or system by spin refrigeration polarisation. The system is doped with or intimately mixed with suitable paramagnetic materials such as $Ni^{2+}$, lanthanide or actinide ions in crystal form with a symmetry axis of order three or more. The instrumentation is simpler than required for DNP with no need for a uniform magnetic field since no resonance excitation field is applied. The process is carried out by physically rotating the sample around an axis perpendicular to the direction of the magnetic field. The pre-requisite for this method is that the paramagnetic species has a highly anisotropic g-factor. As a result of the sample rotation, the electron paramagnetic resonance will be brought in contact with the nuclear spins, leading to a decrease in the nuclear spin temperature. Sample rotation is carried out until the nuclear spin polarisation has reached a new equilibrium.

The DNP method is the most preferred method for hyperpolarisation according to the invention.

Some of the hyperpolarisation techniques described above, e.g. DNP, brute force or spin refrigeration transfer, are advantageous when transferring polarisation to a sample in the solid state. If the sample is not solid, it may conventionally be frozen in an appropriate solvent or solvent mixture prior to hyperpolarisation by one of the methods that need to be carried out in the solid state. Solvent mixtures have been found to be particularly suitable, especially if the mixture forms an amorphous glass, e.g. comprising glycerol, propanediol or glycol. Such an amorphous matrix is preferably employed in DNP hyperpolarisation to ensure homogenous distribution of the compounds in the solid.

The polarisation of the NMR active nuclei can be measured by its enhancement factor compared to thermal equilibrium at the spectrometer field and temperature. Suitably, the enhancement factor for any NMR active nucleus is at least 10, preferably at least 50 and more preferably at least 100.

If hyperpolarisation is carried out by a method that requires the sample to be in the solid state, the at least one hyperpolarised ligand or the hyperpolarised target is preferably brought into solution after the hyperpolarisation step. Suitable solvents are those which are useful to study the interaction between ligand and target in step b) and c) of the method according to the invention. Such solvents are for example non-deuterated and deuterated buffers, like phosphate buffers and they may contain small amounts of organic solvents such as DMSO, methanol and acetic acid.

In the method according to the invention, the hyperpolarised compounds (i.e. ligand(s) or target) are contacted with non-hyperpolarised compounds (i.e. ligand(s) or target) to form a mixture. The amount of hyperpolarised ligand/target required depends on the enhancement factor, the kind of information the assay should provide and the line width of the peaks.

If the hyperpolarised compound is a ligand, then said ligand is contacted with either a target or with a target and at least one further ligand which is different from the hyperpolarised ligand. In the first case, it is for example possible to investigate whether a specific ligand binds to a target, obtaining information about the affinity of the ligand, e.g. by calculating binding constants, binding distances and/or obtaining structural information such as the relative orientation of the bound ligand with respect to the target molecule or the identification of epitopes on the target the ligand binds to. It is further possible to identify for example a potent inhibitor of an enzyme, e.g. if the hyperpolarised ligand is a known substrate for an enzyme (target) and the mixture contains a plurality of putative inhibitors (ligands), by monitoring changes in the conversion rate of the enzyme. In the second case, it is for example possible to hyperpolarise a known ligand for a specific target and thus identify ligands with higher affinity to the target from a plurality of different ligands. Information about the affinity of the bound ligand is obtained, e.g. by calculating binding constants and/or obtaining structural information such as binding distances, the relative orientation of the bound ligand with respect to the target molecule or the identification of epitopes on the target the ligand binds to.

If more than one ligand is hyperpolarised, then said ligands are contacted with a target to form a mixture. Thus, it is possible to identify the ligand with the highest affinity to a specific target among a plurality of different ligands, e.g. a ligand library. It is further possible to obtain information about the affinity of the ligand, e.g. by calculating binding constants and/or obtaining structural information such as binding distances, the relative orientation of the bound ligand with respect to the target molecule or the identification of epitopes on the target the ligand binds to.

If the hyperpolarised compound is a target, then said target is contacted with at least one ligand. Thus, it is possible to investigate whether a specific ligand binds to the target or to identify the ligand with the highest affinity to the target among a plurality of different ligands, e.g. a ligand library. It is further possible to obtain information about the affinity of the ligand, e.g. by calculating binding constants and/or obtaining structural information such as binding distances, the relative orientation of the bound ligand with respect to the target molecule or the identification of epitopes on the target the ligand binds to.

For the formation of the mixture, the hyperpolarised compounds as well as the non-hyperpolarised compounds are preferably dissolved in a suitable solvent, like suitable buffers. In a preferred embodiment, a solution of the hyperpolarised compound is directly transferred into a solution of the non-hyperpolarised compounds. The formation of a mixture can be achieved by several means known in the art, such as stirring, vortexing, sonification, etc.

The NMR spectrum generated from the mixture may be a one-, two- or multidimensional NMR spectrum, preferably a one-dimensional NMR spectrum of the nucleus of choice, like $^{13}C$, $^{15}N$, $^{19}F$, $^{31}P$ or $^{1}H$. The spectrum may be acquired in a single scan or in several scans in any combination of RF and gradient pulses, depending on the NMR parameters to be extracted and the information to be obtained. Such parameters are for example chemical shift, line broadening, dipolar or scalar couplings. In a preferred embodiment, low flip angels are used in the generation of the NMR spectrum. Thus, it is possible to study the dynamic behaviour of the interaction between a ligand and a target or the time dependent fate of a chemical reaction. Further information to be obtained may be binding constants to determine binding affinity, binding distances, or structural information such as the relative orientation of a bound ligand with respect to the target molecule, or the identification of epitopes on the target a ligand binds to. Said structural information may for example be obtained by monitoring transfer NOEs (Nuclear Overhauser Effects) from the hyperpolarised compound (e.g. hyperpolarised $^{13}C$ spins on a ligand) to the non-hyperpolarised compound (e.g. the protons of a target). The NOE from a hyperpolarised nuclear spin to a non-hyperpolarised nuclear spin will result in partial transfer of the large non-equilibrium polarisation from the former to the latter, and thus cause transient enhancement of the corresponding NMR signals. This change in the NMR signal, which can be readily observed using one-dimensional NMR, is a convenient way of mapping dipolar interactions between a hyperpolarised nuclear spin and others. As the NOE can be either intra- or inter-molecular, this technique could be used, for instance, to map the binding site on a target after contacting it with a hyperpolarised ligand. Preferably, the sample is maintained under conditions optimised for longest possible $T_1$, i.e. as high temperature as possible and the use of deuterated solvents.

The NMR spectrum generated from the mixture is compared to a reference spectrum of the at least one hyperpolarised ligand or the hyperpolarised target.

For the reference spectrum of the at least one hyperpolarised ligand or the hyperpolarised target, those compounds are measured in their free state, i.e. before contacted with the target or at least one ligand. The conditions for generating said reference spectrum should be as close to the conditions of generating the NMR spectrum of the mixture. Preferably, the conditions are identical with respect to e.g. solvents, pH and spectral parameters like for instance pulse length. The reference spectrum may be a one-, two- or multidimensional NMR spectrum, preferably a one-dimensional NMR spectrum of the nucleus of choice, e.g. $^{13}C$, $^{15}N$, $^{31}P$, $^{19}F$ or $^{1}H$. The spectrum may be acquired in a single scan or in several scans in any combination of RF and gradient pulses. Preferably, the sample is maintained under conditions optimised for longest possible $T_1$, i.e. as high temperature as possible and the use of deuterated solvents.

Comparison may be done by mere visual assessment of the spectra, e.g. if a peak has appeared or disappeared. Suitably, comparison is carried out in a computer-assisted way, e.g. by calculating a difference spectrum between the NMR spectrum of the mixture and the reference spectrum. Preferably, chemical shift changes, line broadening, relaxation time differences or NOE effect differences may be monitored. If a ligand is in fast or intermediate exchange with the target, the position and width of the monitored NMR signal is affected by exchange broadening. The NMR signal(s) occurs somewhere between the position of the chemical shifts in the free ligand and in the bound ligand and the signal(s) is more or less broadened. When the ligand is tightly bound to the target, such that the "slow exchange limit" applies, two distinct sets of NMR signals will be obtained, namely one set arising from the free fraction of the ligand and one set arising from the bound fraction of the ligand. The relative intensities of these two signals reflect the free and bound fractions of the corresponding ligand. Thus, it is possible to for example identify ligands that bind to the target, identify ligands with higher binding affinities to a target, determine binding constants or to identify potent enzyme inhibitors, agonists or antagonists. It is further possible to obtain structural information about the interaction between the ligand and the target such as binding distances, relative orientation of the ligand with respect to the target molecule or the identification of epitopes on the target the ligand binds to. One way of obtaining structural information of a ligand-target complex by NMR is to exploit throughspace dipolar couplings between nuclear spins of the ligand and of the target, respectively. In the case of one constituent, e.g. either the hyperpolarised ligand or hyperpolarised target, a large non-equilibrium polarisation is present at certain sites. These could be, for instance, one or more $^{13}C$- or $^{15}N$-enriched sites on the ligand. According to the NOE, dipolar coupling between nuclear spins gives rise to cross-relaxation between the coupled spins. Dipolar cross-relaxation may therefore yield partial transfer of the enhanced polarisation from the ligand to the target and vice versa. These cross-relaxation rates, which can be obtained from the transient changes in the nuclear polarisation of the corresponding sites, are a function of the distance between the coupled spins, of the reorientational correlation time, and of the gyromagnetic ratios of the nuclear spins involved. Knowing the latter parameters and observing the NOE induced enhancement pattern of individual NMR signals, it is therefore possible to calculate through-space distances and map the binding sites. Said structural information may for instance be obtained by monitoring transfer NOEs from the hyperpolarised compound (e.g. the hyperpolarised $^{13}C$ spins on a ligand) to the non-hyperpolarised compound (e.g. the protons of a target). Besides pinpointing binding pockets on the target from identification of the interactions involved in the binding, these NOEs reflect binding distances between the ligand and the target.

Another aspect of the invention is the use of hyperpolarised ligand(s) and/or hyperpolarised target(s) in NMR assisted drug discovery, preferably in NMR-based screening and/or optimisation methods in drug discovery, particularly preferably in the method according to the invention.

The hyperpolarised ligand(s) and/or target(s) used may be isotopically enriched. If non-enriched hyperpolarised ligands and/or targets are used, hyperpolarised ligands and/or targets containing nuclear species occurring at high natural abundance such as $^{31}P$, $^{19}F$, and/or $^1H$ are preferred. In a preferred embodiment, the hyperpolarised ligands and/or targets are isotopically enriched, particularly preferably isotopically enriched in such a way as described on page 6 and 7 of the present application.

Yet another aspect of the invention is the use of isotopically enriched hyperpolarised ligands in ligand competition assays.

The enrichment may include either selective enrichments of one or more sites within the ligand molecule or uniform enrichment of all sites. Enrichment can be achieved by chemical synthesis or biological labelling. Suitable techniques are known in the art. Preferably, ligand molecules are selectively isotopically enriched, preferably in positions with long $T_1$ relaxation time. Suitably, ligand molecules according to the invention are isotopically enriched molecules with an enrichment of at least 10%, most suitably at least 25%, preferably at least 75%, most preferably at least 90%, ideally approaching 100%.

In a preferred embodiment of the present invention, the ligands are selectively enriched with $^{13}C$ and/or $^{15}N$, preferably with $^{13}C$ or $^{15}N$, particularly preferred with $^{13}C$.

The ligand competition assay can be used to identify inhibitors, antagonists or agonists of a specific target molecule. Thus, it is possible to identify potent drug compounds.

EXAMPLES

Example 1

SH2 domains are modules of about 100 amino acids that bind to specific phosphotyrosine (pY)-containing peptide motifs. These domains are found in a large number of proteins involved in signal transduction. Because SH2 domains play a fundamental role in a variety of signal transduction pathways, SH2 domains have been the targets of extensive drug design efforts. However, the determinants of pY recognition by SH2 domains are still not well understood. It is thus of interest to identify the attributes of pY required for high affinity interaction with SH2 domains.

The purpose of the experiment was to illustrate the monitoring of chemical shift differences of an enriched ligand between the bound and free state and thereby to determine if binding takes place and to determine the binding affinity.

Target: Src homology domain 2 from growth binding hormone

Ligand: $(1-^{13}C)$—Ac—EpYINQ—$NH_2$

Example 1.1

1.1.1 Acquisition of the Reference Spectrum of the Free Hyperpolarised Ligand 19 nmol ligand was dissolved in 12 μl water and mixed with 15.6 mg of a glycerol solution containing 30 mM trityl radical. The liquid sample was frozen as droplets in liquid nitrogen. The sample was placed in the polariser and hyperpolarised overnight (17 h) at 93.934 GHz and 100 mW (DNP method). The sample was brought into solution with phosphate buffer (pH 6.5, 100 mM, 60° C., 8.5 ml). The active dissolution volume was 3 ml with 90% recovery of substance, providing a final concentration of 5.7 μM. The dissolved ligand was injected directly into a 10 mm NMR tube and quickly transferred to a 9.4 T magnet, with the probe at 25° C. A liquid state NMR spectrum was acquired in one scan with a 90° pulse angle and acquisition time of 1 s. One NMR signal was obtained at 176.9 ppm from the $^{13}C$-labeled ligand. The signal-to-noise ratio (SNR) of the spectrum was 50.

1.1.2 Preparation of the Target Solution

940 μl of the target solution (100 μM target, 5 mM DTT, 100 mM NaCl, 50 mM phosphate pH 6.5) was placed in 10 mm NMR tube with a bottom plug, reducing the active volume to 1100 μl. The tube was placed in a 9.4 T magnet with the temperature of the probe equilibrated to 25° C. A tube was connected to the bottom of the NMR tube to allow for injection of the ligand solution into the target solution.

1.1.3 Hyperpolarisation of the Ligand and Formation of the Target/Hyperpolarised Ligand Mixture 0.32 μmol ligand was dissolved in 20 μl water and mixed (1:1 w/w) with a glycerol solution containing 30 mM trityl. The liquid sample was frozen as droplets in liquid nitrogen. The sample was placed in the polariser and hyperpolarised overnight (17 h) at 93.934 GHz and 100 mW (DNP method). The dissolution was performed with phosphate buffer (pH 6.5, 100 mM, 50° C., 7 ml). Active dissolution volume was 1.5 ml with about 70% recovery of substance. A 1 ml syringe was filled completely (volume: 1100 μl) with the ligand solution, a total of 160 μl of the ligand solution was quickly injected into the target solution, resulting in a total ligand concentration of 24 μM.

1.1.4 Acquisition of an NMR Spectrum of the Mixture

A NMR spectrum was generated using the same spectral parameters as for the reference spectrum. Acquisition time was 1 s, the SNR was 20. The NMR spectrum showed two signals, one from the unbound ligand (176.94 ppm) and one from the bound ligand (176.2 ppm).

In this example, the target to ligand concentration ratio was 4:1. Since the ligand is known to be in slow exchange with the target, it was expected that both a signal of the free ligand and a signal of the bound ligand would be seen. By varying the ligand to target concentration in the assay it would thus be possible to measure the binding affinity by quantifying the relative amounts of free and bound ligand visible in the spectra based on the knowledge of ligand/target concentrations used in the assay.

Comparison Example 1.2

For a sensitivity comparison, the same experiment was performed with conventional NMR. ID $^{13}$C-NMR spectra of the ligand in the free state and in a mixture with the target were acquired with a $^{13}$C frequency of 75.436 MHz on a Varian INOVA. Data was collected with 32 k data points, 4096 transients, spectral width of 20000 Hz and an acquisition time of 800 ms. The concentration of the ligand was 0.8 mM. The concentration of the ligand and target in the mixture was 0.6 mM each. Total acquisition time was about 8 hours for each spectrum and the signals in the resulting spectra were barely detectable.

In the method of the invention (example 1.1) a 30 times lower ligand concentration can be used compared to the ligand concentration in conventional methods (example 1.2). Further, the acquisition time of the NMR spectra according to the method of the invention is extremely short (1 s compared to 8 hours), this will consequently place less requirement on stability to the system. The spectra showed a higher SNR than the spectra acquired in the conventional method.

Example 2

Depending on the on/off rate of a binding ligand among other ligands, the NMR spectrum of the ligands/target mixture will show changes (chemical shift changes or line broadening) compared to the spectrum of the free ligand mixture. A difference spectrum will thus reveal the binder in the mixture as being the compound that changes one of these properties upon binding to the target. In this example the line broadening of the ligand signal indicates binding to the target.

The purpose of the experiment was to illustrate the identification of a non-enriched binder in a mixture of non-enriched ligands.

Target: Human Serum Albumin

Ligands: salicylic acid and ascorbic acid.

It is known that salicylic acid binds with μM affinity to the target while ascorbic acid binds with mM affinity.

Example 2.1

2.1.1 Acquisition of the Reference Spectrum of the Free Hyperpolarised Ligands 5 mg ascorbic acid and 5 mg salicylic acid were dissolved in 1 ml water. 20 μl of this solution was mixed with 26 mg of a glycerol solution containing 30 mM trityl radical. The liquid sample was frozen as droplets in liquid nitrogen and hyperpolarised in 6 hours (DNP method). The dissolution was performed with phosphate buffer (pH 7.6, 100 mM, 60° C., 8.5 ml). Active dissolution volume was 3 ml (90% recovery of substance), providing a final concentration of 0.17 mM with respect to ascorbic acid and 0.19 mM with respect to salicylic acid. The solution was transferred directly into a 10 mm tube and quickly transferred to the 9.4 T magnet. Acquisition time was 1 s, the SNR was 55. The spectrum showed signals originating from both the ascorbic acid and salicylic acid.

2.1.2 Hyperpolarisation of the Ligands, Mixing with the Target and Acquisition of a NMR Spectrum of the Mixture The preparation of the ligands and the hyperpolarisation was carried out as described in 2.1. The ligand solution was directly injected into a 10 mm tube containing 10 mg of human serum albumin (final concentration 50 μM, about ¼ of the amount of ligands present). A NMR spectrum was acquired under the same conditions as described in 2.1, the SNR was 50.

In this spectrum the signals from the salicylic acid disappeared upon binding to the target due to exchange broadening. The signals from the weaker binder ascorbic acid remained in the spectrum.

Comparison Example 2.2

For a sensitivity comparison, the same experiment was performed with conventional NMR. Two samples were prepared, one reference sample with 1 mM of each ligand in phosphate buffer pH 7.5 and one sample of the target/ligands mixture with the same amount of ligands and 0.2 mM target. Two-dimensional $^1$H—$^{13}$C-HSQC spectra of each sample were acquired on a Bruker Avance 500 MHz NMR spectrometer equipped with an inverse triple resonance probe. The HSQC type spectrum was acquired as a directly detected carbon spectrum could not be performed within a reasonable time frame. Acquisition of each spectrum took 10 hours and the obtained signals were barely detectable. The reference sample showed the expected signals for both ligands. The sample of the target/ligands mixture showed signals only for the low affinity ligand ascorbic acid. The signals from salicylic acid were broadened beyond detection due to exchange broadening.

Again, with conventional methods much higher ligand concentrations had to be used. Acquisition time is extremely long (10 hours compared to 1 s) and SNR is low (3 compared to 50).

Example 3

The same ligands/target as in example 2 were used with the exception that $^{13}$C-enriched salicylic acid was used. Thus, only the fate of the labeled ligand was monitored as an indicator for the presence/absence of a higher affinity ligand present in a ligand mixture.

The purpose of the experiment was to illustrate the monitoring of the displacement of an isotope-labeled binder by a higher affinity binder from a pool of non-binding ligands.

3.1 Acquisition of a Reference Spectrum of the Free $^{13}$C Labeled Salicylic Acid 5 mg salicylic acid ($^{13}$C labeled in carbonyl position) was dissolved in 100 ml water. 20 μl of this solution were mixed with 26.6 mg glycerol solution containing 30 mM trityl radical. The liquid sample was frozen as droplets in liquid nitrogen. The sample was hyperpolarised overnight (17 hours) (DNP method). The sample was dissolved in buffer (100 mM phosphate buffer pH 7.6, 60° C., 8.5 ml), collected in a 10 mm tube and quickly transferred to a 9.4 T magnet. A single-scan ID solution $^{13}$C-NMR spectrum was collected (acquisition time: 1 s, 90° pulse). The spectrum showed a single peak from salicylic acid, SNR was 40. This SNR is expected according to the 100-fold dilution of the $^{13}$C-enriched material compared to the NMR experiment using the natural abundance $^{13}$C-material in 2.1.1.

3.2 Hyperpolarisation of $^{13}$C Labeled Salicylic Acid, Mixing with the Target and the Second Ligand Ascorbic Acid and Acquisition of a NMR Spectrum of the Mixture The preparation of the $^{13}$C labeled salicylic acid and the hyperpolarisation were carried out as described in 3.1. After dissolution the sample was collected in a 10 mm NMR tube containing a concentrated solution of target and the second ligand ascorbic acid. The NMR tube was quickly transferred to the magnet and a NMR spectrum was generated as described in 3.1. No peaks were visible in the spectrum indicating that the signal from salicylic acid had broadened beyond detection as a consequence of its binding to the target.

The experiment could be carried out in the same way, but instead of ascorbic acid, which is a weaker binder than salicylic acid, a ligand having a higher binding affinity than salicylic acid could be used. The spectrum acquired from the mixture would show a signal from the labeled salicylic acid indicating that a competition had taken place since the ligand with higher affinity was bound to the target and salicylic acid would thus be free in solution.

In conclusion, this assay showed that a signal from a labeled ligand appeared in the spectrum when a ligand with a higher binding affinity was present whereas the signal disappeared when only ligands with lower affinity than the labeled ligand were present.

Example 4

A robust and fast screening assay for inhibitors may be of great importance in drug therapy. That this is the case can be illustrated by the human pathogen, *Helicobacter pylon*. This pathogen plays a prominent role in the pathogenesis of peptic ulcer and gastric cancer. The bacterium contains the enzyme urease (an enzyme that is not present in higher animals). Urease catalyses the hydrolysis of urea to ammonia and carbamate. Ammonia generated by urease elevates the pH in the stomach and thereby protects the bacterium. The present available therapy uses a combination of antibiotics and proton pump inhibitors. Because of the emergence of antibiotic resistant strains there is an urgent need for novel treatment. A possibility is inhibition of the potent urease activity of *H. pylori*.

The purpose of the experiment was to illustrate the identification a potent enzyme inhibitor in a mixture of ligands with unknown binding characteristics by monitoring changes in the conversion rate in an enzymatic reaction.

Enzyme (target): Urease

Substrate (ligand): $^{13}$C-labeled urea 4.1 Acquisition of a Reference Spectrum Showing the Enzymatic Conversion of $^{13}$C-Labeled Urea as a Function of Time 16.4 µmol of $^{13}$C-labeled urea was mixed 1:1 (w/w) with a glycerol solution containing 30 mM trityl radical. The liquid sample was frozen as droplets in liquid nitrogen. The frozen sample was hyperpolarised for one hour (DNP method). The sample was dissolved in a phosphate buffer (10 mM, pH 7.6, 100° C., 8.5 ml (active dissolution volume 3 ml)) and 500 µl were transferred to a 10 mm NMR tube containing 2.5 ml of a solution (same buffer as for urea) containing 12 units urease (0.1 mg). A series of 40 one-dimensional $^{13}$C spectra were collected as one every 3 s, with a reduced flip angle (15°). The resulting spectra showed the conversion of the substrate as a function of time, i.e. the formation of the intermediate product carbon dioxide and subsequently the formation of the end product bicarbonate.

4.2 Calculation of the Reaction Rate

It is possible to calibrate the flip angle, and the relaxation rate for urea is known. Hence, the decay of the substrate signal can be used to calculate the rate of the enzymatic conversion (reaction rate). Another way of calculating the reaction rate for the system is to vary the enzyme concentration while keeping the concentration of substrate constant.

The latter approach was used in a series of experiments that were performed as described above, only the concentration of urease was varied. Three experiments were performed with 10 units, 12 units and 14 units urease. The urease activity was plotted as a function of concentration. From this plot, the reaction rate constant was extracted directly. The NMR signal intensities of urea in the individual experiments have been used to calculate the enzymatic activity. Based on these experiments the rate constant for the system was determined to be $k=0.0019$ s$^{-1}$.

4.3 Determination of the $LC_{50}$ Value of the Urease Inhibitor Acetohydroxamic Acid A new series of experiments were performed in order to test the system as a possible screen for enzyme inhibitors. In these experiments both substrate (urea) and enzyme concentration were kept constant and acetohydroxamic acid, a compound that is known to be a urease inhibitor was added in varying concentrations.

Experiments were carried out as described in 4.1 with the NMR tube containing 2.5 ml solution of 12 units urease (0.1 mg) and acetohydroxamic acid. Four experiments were carried out varying the acetohydroxamic acid concentration from about $10^{-6}$-$10^{-4}$ M. As described above the activity was calculated using the NMR intensities of the urea signal in the 4 experiments. By plotting the activity as a function of the varied acetohydroxamic acid concentration, it was possible to determine the concentration of acetohydroxamic acid needed to inhibit the enzyme reaction to half activity ($LC_{50}$ value). From this plot the $LC_{50}$ value was estimated to be $5 \cdot 10^{-5}$M.

Example 5

In order to obtain more specific structural information on the interaction between the ligand and the target and at the same time preserve the high sensitivity of the screening assay it may be possible to observe changes in the target instead of the ligand.

The purpose of the experiment was to either illustrate the detection of a binder in a mixture of non-binders by monitoring chemical shift changes in the target upon binding of the ligand or to pinpoint the involved residues in the target binding site.

In a conventional SAR-by-NMR assay (see Shuker et al. Science 274 (1996), 1531-1534), the aims are to detect a ligand from a pool of ligands that binds to a target, to characterise the binding site in the target, and to measure binding affinity. The binding is determined by the observation of $^{15}$N or $^1$H-amide chemical shift changes in 2D $^{15}$N/$^1$H-HSQC spectra. A reference spectrum of the target alone is compared to the spectrum of the target/ligands mixture. Deconvolution is subsequently used to identify the particular ligand-target interaction.

The steps in a 1D SAR-by-NMR assay according to the invention are the following:

5.1 Acquisition of the Reference Spectrum

After hyperpolarisation of the target (DNP method), the target sample is dissolved in buffer and a 1D solution $^{15}$N-NMR spectrum is collected. This spectrum serves as a reference spectrum.

5.2 Hyperpolarisation of the Target, Formation of a Target/Ligands Mixture and Acquisition of a NMR Spectrum of said Mixture After hyperpolarisation of the target, the target sample is dissolved in buffer and transferred to a mixture of ligands (=potential binders). A 1D solution $^{15}$N-NMR spectrum is collected and compared to the reference spectrum. The difference spectrum reveals chemical shift changes if a ligand that binds to the target was present in the ligand mixture.

Depending on the prior knowledge of the target in the assay, the chemical shift changes may provide structural information.

Example 6

An intra-molecular transfer of polarisation from a $^{13}$C natural abundance carbon to protons adjacent sites in the same molecule has been obtained utilising the NOE effect.

A 50 mg sample of 1,1-Bis(hydroxymethyl)cyclopropane containing 15 mM trityl radical was polarised by the DNP method on $^{13}$C in the solid state at 93.91 GHz and 100 mW. After dissolution in D$_2$O the sample was transferred to the 9.4 T magnet and a $^1$H-NMR spectrum was acquired. During the transport of the sample (after the dissolution until the NMR spectrum is acquired) the protons are polarised negatively due to the polarisation transfer from the attached $^{13}$C that is positively polarised by DNP in the solid state. The transfer mechanism is through the Overhauser effect, i.e. relaxation driven. The enhancement of the protons directly attached to $^{13}$C was measured to ca. 200 times.

The invention claimed is:

1. An NMR-based method comprising the steps of:
   a) hyperpolarising at least one of a ligand and a target, wherein said at least one of a ligand and a target is isotopically enriched with at least one of $^{12}$C and $^{15}$N NMR active nuclei,
   b) forming a mixture by contacting either the at least one hyperpolarised ligand with one of a target and both a target and at least one further ligand or the hyperpolarised target with at least one ligand,
   c) generating a NMR spectrum of the mixture, and
   d) comparing said NMR spectrum with a reference spectrum of the at least one hyperpolarised ligand or the hyperpolarised target.

2. The method according to claim 1, wherein the at least one ligand is selected from the group consisting of proteins, glycoproteins, lipoproteins, polypeptides, glyco-polypeptides, lipopolypeptides, peptides, carbohydrates, nucleic acids or a part, a fragment or a complex thereof and small organic molecules.

3. The method according to claim 1, wherein the at least one ligand is a small organic molecule of less than 2000 Da.

4. The method according to claim 1, wherein more than one hyperpolarised ligand is used.

5. The method according to claim 1, wherein the target is selected from the group consisting of proteins, glycoproteins, lipoproteins, nucleic acids, polypeptides, glycopolypeptides, lipopolypeptides, peptides or a part, a fragment or a complex thereof.

6. The method according to claim 1, wherein the enrichment is a *hu* 13C-enrichment.

7. The method according to claim 1, wherein the NMR spectrum generated is a one-dimensional NMR spectrum.

8. The method according to claim 1, wherein the NMR spectrum generated is generated using low flip angles.

9. The method according to claim 1, wherein the comparison with the reference spectrum shows a chemical shift difference, a relaxation time difference or a NOE effect difference.

* * * * *